US00PP23049P2

(12) United States Plant Patent
Westhoff

(10) Patent No.: US PP23,049 P2
(45) Date of Patent: Sep. 18, 2012

(54) ***VERBENA* PLANT NAMED 'WESVEREVOSTAR'**

(50) Latin Name: *Verbena tenera*
Varietal Denomination: Wesverevostar

(75) Inventor: Heinrich Westhoff, Südlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 13/065,896

(22) Filed: Mar. 31, 2011

(51) Int. Cl.
*A01H 5/00* (2006.01)

(52) U.S. Cl. ..... Plt./308

(58) Field of Classification Search ..... Plt./308
See application file for complete search history.

*Primary Examiner* — Annette Para
(74) *Attorney, Agent, or Firm* — C. A. Whealy

(57) ABSTRACT

A new and distinct cultivar of *Verbena* plant named 'Wesverevostar', characterized by its compact and mounding plant habit; vigorous growth habit; medium-sized leaves; freely flowering habit; red-colored flowers with a light red-colored radiating star pattern; and flowers held above and beyond the foliar plane in rounded umbels.

1 Drawing Sheet

Botanical designation: *Verbena tenera.*
Cultivar denomination: 'WESVEREVOSTAR'.

BACKGROUND OF THE INVENTION

The present invention relates to a new and distinct cultivar of *Verbena* plant, botanically known as *Verbena tenera*, and hereinafter referred to by the name 'Wesverevostar'.

The new *Verbena* plant is a naturally-occurring branch mutation of *Verbena tenera* 'Wesverevoo', disclosed in U.S. Plant Pat. No. 21,620. The new *Verbena* plant was discovered and selected by the Inventor within a population of plants of 'Wesverevoo' in a controlled greenhouse environment in Südlohn, Germany in August, 2008.

Asexual reproduction of the new *Verbena* plant by terminal cuttings in a controlled greenhouse environment in Südlohn, Germany since October, 2008 has shown that the unique features of this new *Verbena* plant are stable and reproduced true to type in successive generations.

SUMMARY OF THE INVENTION

Plants of the new *Verbena* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Wesverevostar'. These characteristics in combination distinguish 'Wesverevostar' as a new and distinct *Verbena* plant:

1. Compact and mounding plant habit.
2. Vigorous growth habit.
3. Medium-sized leaves.
4. Freely flowering habit.
5. Red-colored flowers with a light red-colored radiating star pattern.
6. Flowers held above and beyond the foliar plane in rounded umbels.

Plants of the new *Verbena* can be compared to plants of the parent, 'Wesverevoo'. Plants of the new *Verbena* differ primarily from plants of 'Wesverevoo' in flower color as plants of 'Wesverevoo' have solid red-colored flowers.

Plants of the new *Verbena* can be compared to plants of the Verbena 'Wesvereme', disclosed in U.S. Plant Pat. No. 21,637. In side-by-side comparisons conducted in Südlohn, Germany, plants of the new *Verbena* differed primarily from plants of 'Wesvereme' in the following characteristics:

1. Plants of the new *Verbena* were not as compact as plants of 'Wesvereme'.
2. Plants of the new *Verbena* had longer internodes than plants of 'Wesvereme'.
3. Plants of the new *Verbena* had smaller flowers and inflorescences than plants of 'Wesvereme'.
4. Plants of the new *Verbena* and 'Wesvereme' differed in flower color as plants of 'Wesvereme' had dark red purple-colored flowers.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena* plant.

The photograph at the top of the sheet comprises a side perspective view of a typical flowering plant of 'Wesverevostar' grown in a container.

The photograph at the bottom of the sheet is a close-up view of a typical flowering plant of 'Wesverevostar'.

DETAILED BOTANICAL DESCRIPTION

The aforementioned photographs and following observations, measurements and values describe plants grown during the summer in 12-cm and 25-cm containers in a glass-covered greenhouse in Südlohn, Germany and under conditions which closely approximate commercial production. During the production of the plants, day temperatures ranged from 20° C. to 25° C., night temperatures ranged from 16° C. to 18° C. and light levels ranged from 3,000 to 50,000 lux. Plants were 27 weeks old when the photographs and the description were taken. In the description, color references are made to The Royal Horticultural Society Colour Chart, 2001 Edition, except where general terms of ordinary dictionary significance are used.

Botanical classification: *Verbena tenera* 'Wesverevostar'.

Parentage: Naturally-occurring branch mutation of *Verbena tenera* 'Wesverevoo', disclosed in U.S. Plant Pat. No. 21,620.

Propagation:

*Type*.—Terminal cuttings.

*Time to initiate roots, summer*.—About 14 days at 20° C.

*Time to initiate roots, winter*.—About 16 to 18 days at 20° C.

*Time to produce a rooted cutting, summer*.—About 21 to 24 days at 20° C.

*Time to produce a rooted cutting, winter*.—About 24 to 26 days at 20° C.

*Root description*.—Fibrous, medium in thickness; color, close to 158A.

*Rooting habit*.—Freely branching; moderately dense to dense.

Plant description:

*Plant habit*.—Initially upright, then compact and mounding growth habit; freely branching habit with two lateral branches potentially forming at every node; pinching enhances lateral branch development; dense and bushy plant habit; vigorous growth habit.

*Plant height*.—About 22 cm to 25 cm.

*Plant diameter*.—About 64 cm.

Lateral branch description:

*Length*.—About 27 cm to 50 cm.

*Diameter*.—About 1.9 mm to 2.7 mm.

*Internode length*.—About 2.2 cm to 2.5 cm.

*Texture*.—Densely pubescent.

*Color*.—Close to 144A.

Foliage description:

*Arrangement*.—Opposite, simple; sessile.

*Length*.—About 4.2 cm to 5 cm.

*Width*.—About 2.1 cm.

*Shape*.—Ovate.

*Apex*.—Acute.

*Base*.—Attenuate.

*Margin*.—Dentate to crenate.

*Texture, upper and lower surfaces*.—Densely pubescent.

*Venation pattern*.—Pinnate.

*Color*.—Developing leaves, upper surface: Close to 147A to 147B. Developing leaves, lower surface: Close to 147B. Fully expanded leaves, upper surface: Close to 147A; venation, close to 147B. Fully expanded leaves, lower surface: Close to 147B; venation, close to 147C.

Flower description:

*Flower arrangement and habit*.—Sessile salverform flowers arranged in hemispherical terminal umbels; umbels dense and mounding; numerous umbels covering the entire plant; flowers face upward or outward; freely flowering habit with about 25 to 40 flowers per inflorescence; flowers not persistent.

*Natural flowering season*.—Plants flower continuously from April until frost in the fall in Germany; plants begin flowering about 12 to 14 weeks after planting.

*Fragrance*.—None detected.

*Inflorescence size*.—Diameter: About 5.9 cm. Height: About 2.7 cm.

*Flowers*.—Appearance: Flared trumpet, corolla fused, five-parted; sessile. Length: About 2.3 cm to 2.5 cm. Diameter: About 1.9 cm to 2 cm. Tube length: About 1.8 cm. Throat diameter: About 2.6 mm. Tube diameter, base: About 1.6 mm.

*Flower buds*.—Length: About 1.6 cm to 2 cm. Diameter: About 4 mm to 6 mm. Shape: Oblong. Color: Towards the apex, close to 46B with spots, close to 38B; midsection, close to 145B; base, close to 145C.

*Corolla*.—Arrangement: Single whorl of five fused petals. Petal lobe length: About 9 mm to 10 mm. Petal lobe width: About 9.5 mm. Petal lobe shape: Broadly ovate to cordate. Petal lobe apex: Emarginate. Petal margin: Entire. Petal texture, upper and lower surfaces: Smooth, glabrous; velvety. Color: Petal, when opening, upper surface: Close to 45B; radiating stripes, close to 37B. Petal, when opening, lower surface: Close to 47B; radiating stripes, close to 37C. Petal, fully opened, upper surface: Close to 46B; radiating stripes, close to 36D; main color becoming closer to 45B and stripes, closer to 37B with development. Petal, fully opened, lower surface: Close to 47B to 47C; radiating stripes, close to 36D; main color becoming closer to 45B and stripes, closer to 37B with development. Throat: Close to 145D. Tube: Close to 145C to 145D.

*Calyx*.—Arrangement: Star-shaped calyx with five fused sepals. Sepal length: About 1.2 cm. Sepal width: About 2.4 mm. Sepal shape: Lanceolate. Sepal apex: Acute. Sepal margin: Entire. Sepal texture, upper and lower surfaces: Pubescent; velvety. Sepal color, upper and lower surfaces: Close to 146A to 146C.

*Peduncles*.—Length: About 2.2 cm to 8 cm. Diameter: About 2.1 mm. Strength: Strong; wiry. Texture: Pubescent. Color: Close to 146A.

*Reproductive organs*.—Stamens: Quantity/arrangement: Four per flower, adnate to corolla tube. Anther shape: Two-parted; ovate. Anther length: About 1.5 mm. Anther diameter: About 1.1 mm. Anther color: Close to 1C. Pollen amount: Scarce. Pollen color: Close to 1B. Pistils: Quantity: One per flower. Pistil length: About 1.8 cm. Stigma shape: Ovate. Stigma color, immature: Close to 146A. Stigma color, mature: Close to 146B. Style length: About 1.5 cm. Style color: Close to 145C. Ovary color: Close to 145B. Seeds: Length: About 5 mm. Diameter: About 1.3 mm. Color: Close to 197A.

Temperature tolerance: Plants of the new *Verbena* have been observed to tolerate temperatures from about 5° C. to about 30° C.

Pathogen/pest resistance: Plants of the new *Verbena* have not been observed to be resistant to pathogens and pests common to *Verbenas*.

It is claimed:

1. A new and distinct *Verbena* plant named 'Wesverevostar' as illustrated and described.

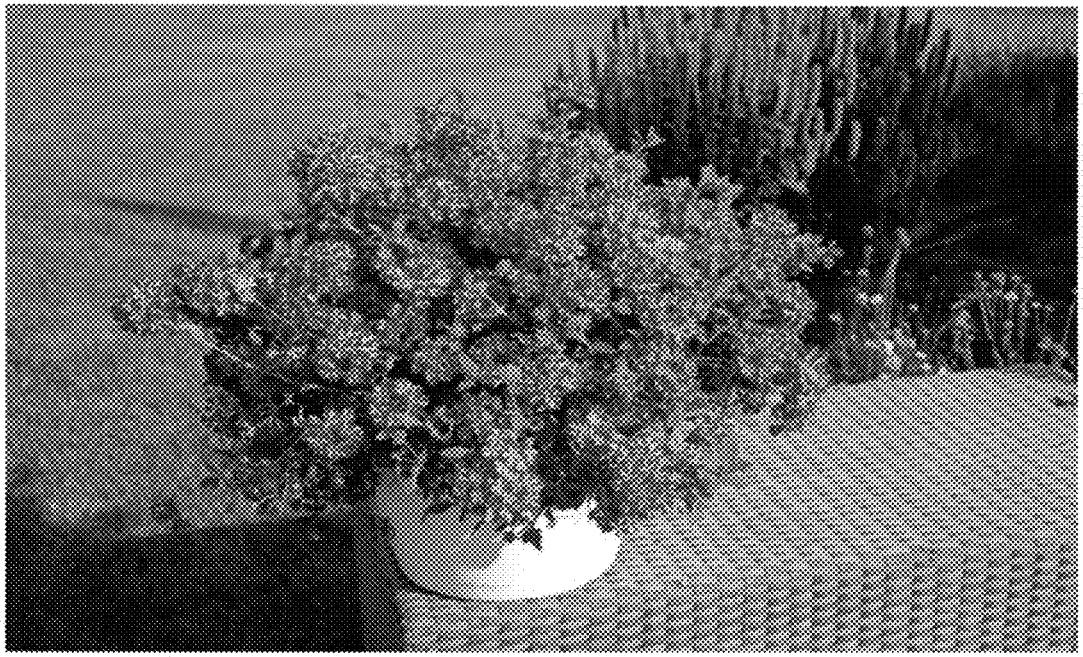
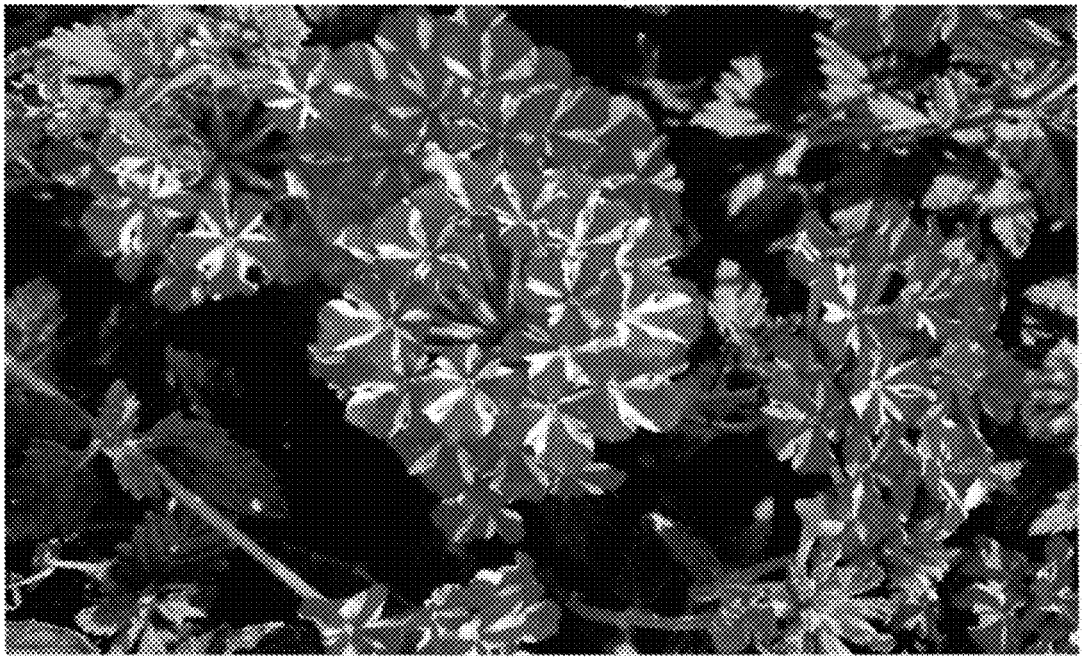

* * * * *